United States Patent
Albert et al.

(10) Patent No.: US 10,099,992 B2
(45) Date of Patent: Oct. 16, 2018

(54) METHOD FOR SEPARATING FORMIC ACID FROM A REACTION MIXTURE

(71) Applicant: OXFA GMBH, Scheßlitz (DE)

(72) Inventors: Jakob Albert, Marloffstein (DE); Andreas Bösmann, Heßdorf (DE); Jenny Reichert, Erlangen (DE); Peter Wasserscheid, Erlangen (DE)

(73) Assignee: OXFA GMBH, Scheßlitz (DE)

( * ) Notice: Subject to any disclaimer, the term of this patent is extended or adjusted under 35 U.S.C. 154(b) by 0 days.

(21) Appl. No.: 15/544,443

(22) PCT Filed: Jan. 18, 2016

(86) PCT No.: PCT/EP2016/050903
§ 371 (c)(1),
(2) Date: Jul. 18, 2017

(87) PCT Pub. No.: WO2016/116405
PCT Pub. Date: Jul. 28, 2016

(65) Prior Publication Data
US 2017/0369413 A1    Dec. 28, 2017

(30) Foreign Application Priority Data
Jan. 19, 2015  (EP) ........................... 15151654

(51) Int. Cl.
*C07C 51/48*  (2006.01)
*C07C 53/02*  (2006.01)

(52) U.S. Cl.
CPC ............. *C07C 51/48* (2013.01); *C07C 53/02* (2013.01)

(58) Field of Classification Search
None
See application file for complete search history.

(56) References Cited

U.S. PATENT DOCUMENTS

| | | | |
|---|---|---|---|
| 6,713,649 B1 | 3/2004 | Hladiiy et al. | |
| 8,492,586 B2* | 7/2013 | Reunanen | C07C 51/44 549/489 |
| 8,530,695 B2* | 9/2013 | Reunanen | C07C 51/44 549/489 |
| 8,759,575 B2* | 6/2014 | Bosmann | C07C 51/23 562/515 |
| 2011/0098490 A1* | 4/2011 | Reunanen | C07C 51/44 549/498 |
| 2011/0137051 A1* | 6/2011 | Reunanen | C07C 51/44 549/489 |
| 2013/0245319 A1* | 9/2013 | Bosmann | C07C 51/23 562/531 |
| 2014/0316161 A1* | 10/2014 | Mullen | C07C 51/00 562/577 |

FOREIGN PATENT DOCUMENTS

| | | |
|---|---|---|
| EP | 1 230 206 B1 | 2/2004 |
| EP | 2 473 467 B1 | 9/2013 |
| WO | WO 2009/130386 * | 10/2009 |
| WO | 2013/078391 A1 | 5/2013 |

OTHER PUBLICATIONS

International Search Report issued in PCT/EP2016/050903 dated Mar. 18, 2016.
Khenkin A. M. et al., "Oxidative C—C Bond Cleavage of Primary Alcohols and Vicinal Diols Catalyzed by H5PV2Mo10O40 by an Electron Transfer and Oxygen Transfer Reaction Mechanism", J. Am. Chem. Soc. 2008, 130, 14474 to 14476.
English translation, International Preliminary Report on Patentability, International Application No. PCT/EP2016/050903 (published as WO 2016/116405), dated Jun. 2, 2017 (5 pages).

* cited by examiner

*Primary Examiner* — Jafar F Parsa
*Assistant Examiner* — Amy C Bonaparte
(74) *Attorney, Agent, or Firm* — Prismatic Law Group PLLC

(57) ABSTRACT

The invention relates to a method for separating formic acid from a reaction mixture which comprises, in addition to formic acid, a polyoxometalate ion of general formula $[PMo_xV_yO_{40}]^{n-}$, where $6 \leq x \leq 11$, $1 \leq y \leq 6$, $x+y=12$ and $3 < n < 10$, where n, x and y are each integers, wherein the separation occurs by means of an extraction using a linear primary alcohol, wherein the carbon chain of the alcohol comprises 5 to 12 carbon atoms, and the reaction mixture is present in a protic solvent.

11 Claims, No Drawings

METHOD FOR SEPARATING FORMIC ACID FROM A REACTION MIXTURE

The present invention is filed under 35 U.S.C. § 371 as the U.S. national phase of International Patent Application No. PCT/EP2016/050903, filed Jan. 18, 2016, which designated the United States and which claims priority to European Patent Application No. 15151654.9 filed Jan. 19, 2015, each of which is hereby incorporated in its entirety including all tables, figures and claims.

The invention relates to a method for separating formic acid from a reaction mixture comprising a polyoxometalate ion in addition to the formic acid.

Such a method is known from EP 2 473 467 B1, where the formic acid can be separated by extraction. An ether or an amide may be used for the extraction.

EP 1 230 206 B1 describes a method for producing formic acid in which methyl formate is hydrolyzed and the methanol and the excess methyl formate are separated by distillation, yielding aqueous formic acid. The aqueous formic acid is then extracted with at least one formic acid ester from the group formed by ethylene glycol diformate, diethylene glycol diformate, 1,2-propanediol diformate, 2,3-propanediol diformate, dipropylene glycol diformate 2,3-butanediol diformate, 1,4-butanediol diformate, benzyl formate, cyclohexyl formate, 2-phenyl formate and 2-ethylhexyl formate, yielding a mixture of formic acid esters and formic acid under distillation conditions in an extractive distillation column. The resulting mixture of formic acid esters and formic acid is then separated by distillation. This method is relatively complex because it requires an extractive distillation column and a plurality of distillation steps.

WO 2009/130386 A1 describes a method for obtaining formic acid. In one exemplary embodiment, formic acid is extracted from an aqueous mixture from acid hydrolysis of biomass by means of octanol.

WO 2013/078391 A1 discloses a method for producing levulinic acid, formic acid and/or hydroxymethylfurfural from various biomasses. Various organic solvents were used in the exemplary embodiments, such as, for example, n-hexanol, n-heptanol, n-octanol, 1-nonanol and 1-undecanol for extraction of levulinic acid, formic acid and sulfuric acid from an aqueous solution.

A. M. Khenkin and R. Neumann, J. Am. Chem. Soc. 2008, 130, 14474 to 14476, describe oxidative cleavage of C—C bonds of primary alcohols and vicinal diols such as 1,2-ethanediol. The catalyst used here is $H_5PV_2Mo_{10}O_{40}$. The primary alcohols were converted to dioxotetrahydrothiophene under strictly anaerobic conditions. Linear alcohols with four, five and six carbon atoms were used as the primary alcohols.

The object of the present invention is to provide an alternative method for separation of formic acid from a reaction mixture comprising a polyoxometalate ion in addition to formic acid.

This object is achieved by the features of patent claim 1. Expedient embodiments are derived from the features of patent claims 2 to 9.

According to the invention, a method for separating formic acid from a reaction mixture is provided, wherein the reaction mixture comprises a polyoxometalate ion of the general formula $[PMo_xV_yO_{40}]^{n-}$ in addition to formic acid, where $6 \leq x \leq 11$, $1 \leq y \leq 6$, $x+y=12$, and $3 < n < 10$, where n, x and y each denote an integer. In one embodiment of this method, $n=3+y$. The charge may also assume other values from 4 to 9, depending on the conditions in the reaction mixture, such as pH. Separation is accomplished by extraction by means of a linear primary alcohol, where the carbon chain of the alcohol has 5 to 12 carbon atoms. The reaction mixture is in a protic solvent.

The reaction mixture may be for example a reaction mixture comprised of a method for catalytic production of formic acid. The aforementioned polyoxometalate ion serves as the catalyst. The catalyst may be brought in contact with an α-hydroxyaldehyde, an α-hydroxycarboxylic acid, a carbohydrate or a glycoside as a substrate in a liquid solution at a temperature below 120° C., as described in EP 2 473 467 B1. In addition, the reaction mixture may contain an additive, for example, toluenesulfonic acid, that promotes digestion of the substrate. In reaction of the substrate with the aforementioned catalyst, $CO_2$ is formed to varying extents in addition to formic acid. The method according to the invention allows extraction of formic acid out of this reaction mixture during the reaction to produce formic acid under reaction conditions that are favorable for the reaction, i.e., for example, at a temperature of 50° C. to 120° C., in particular 60° C. to 100° C., in particular 70° C. to 95° C., in particular 85° C. to 95° C. It permits extraction of formic acid out of the reaction mixture without inactivating the catalyst at the same time or extracting it together with the formic acid.

Alternatively, a portion of the reaction mixture may be separated and extracted by means of the aforementioned alcohol, and the remaining solution containing the catalyst may be sent back to the remaining reaction mixture.

Alcohol as the extraction agent has the advantage that it does not inactivate the catalyst and, at any rate, it inhibits the action of the catalyst in the creation of formic acid in the reaction mixture. The extraction may thus be carried out during the production of formic acid in the reaction mixture.

Extraction of formic acid by means of linear primary alcohols is fundamentally known from the prior art. However, those skilled in the art are aware from A. M. Khenkin and R. Neumann, J. Am. Chem. Soc. 2008, 130, 14474 to 14476, that primary alcohols are cleaved by oxidation in the presence of a polyoxometalate catalyst. However, the inventors of the present patent application have discovered that the reaction of primary alcohols by means of the aforementioned polyoxometalate ion, as described by A. M. Khenkin and R. Neumann, J. Am. Chem. Soc. 2008, 130, 14474 to 14476, can be prevented if the reaction mixture is in a protic solvent and not in an aprotic solvent. A linear primary alcohol could not be used for extraction of formic acid under the reaction conditions described in the aforementioned publication because it would then be oxidized in the presence of the catalyst, splitting a C—C bond. However, it has been recognized that linear primary alcohols in protic solvents are also suitable for extraction of formic acid formed in the reaction mixture even in the presence of the aforementioned polyoxometalate ion.

In one embodiment of the invention, the linear primary alcohol has six, seven or eight carbon atoms. It may be 1-hexanol or 1-heptanol, for example.

In one embodiment, the protic solvent is an organic substance or the reaction mixture comprises an organic substance. This may be an α-hydroxyaldehyde, an α-hydroxycarboxylic acid, a carbohydrate or a glycoside, for example.

The α-hydroxyaldehyde, the α-hydroxycarboxylic acid, the carbohydrate or the glycoside may be a monosaccharide, in particular an aldose, a disaccharide, an oligosaccharide or a polysaccharide, starch, cellulose, hemicellulose, glucose, sucrose, xylose, cellobiose, xylan, a hetero-oligosaccharide, a heteropolysaccharide, glycolic acid or lactic acid or a residual substance containing α-hydroxyaldehyde, α-hydroxycarboxylic acid, carbohydrate or glycoside or it may be a raw material, in particular a renewable raw material, in particular untreated. "Untreated" here means that it has not first been chemically digested. The residual substance or the renewable raw material may be a plant, a fungus or bacteria or components of plants, fungi or bacteria, wood, in particular in the form of sawdust or wood shavings, paper, in particular recycled paper, algae, cyanobacteria or silage. The α-hydroxyaldehyde, the α-hydroxycarboxylic acid, the carbohydrate or the glycoside may also comprise a mixture of at least two of the aforementioned substances or it may be formed from at least one of the aforementioned substances or the mixture, as is the case with peat or brown coal, for example. Many of the aforementioned raw materials are obtained as by-products, for example, in papermaking or in the processing of wood.

In one embodiment of the method according to the invention, the solvent product is polar. This means that the electronegativity difference in a bond of atoms of solvent is greater than 0.1, in particular greater than 0.4. The protic solvent may be water, for example.

After extraction, the linear primary alcohol can be separated from at least some of the formic acid and added to the reaction mixture for further extraction of formic acid. The separation of at least some of the formic acid may take place, for example, by distillation or by separation of formic acid by forming a formate. To form a formate, the formic acid may be reacted with a hydroxide, forming a solution of the formate. The linear primary alcohol can be separated by evaporation from the formate, which remains as a solid and can be recovered by subsequent condensation as a liquid and optionally reused for extraction.

The invention is explained in greater detail below on the basis of exemplary embodiments.

In a first exemplary embodiment, a mixture containing 0.91 g (0.5 mmol) $H_8[PV_5Mo_7O_{40}]$ and 10.91 g formic acid (FA) in 50 mL water is extracted for 1 hour at 90° C. while stirring using the various extraction agents listed in Table 1 below. To determine the respective concentration of formic acid in the organic phase and in the aqueous phase, each batch was then transferred to a separating funnel, in which the two phases were separated. Samples of the two phases were then analyzed with the help of $^1$H-NMR in order to determine the formic acid concentration, using benzene as an external standard.

TABLE 1

| Extraction agent | Distribution coefficient K $c_{FA, org}/c_{FA, aqu}$ | Selectivity $K_{FA}/K_{water}$ |
|---|---|---|
| 1-Hexanol | 0.94 | 8.6 |
| 1-Heptanol | 0.67 | 4.4 |
| Di-n-butyl ether | 0.22 | 1.2 |
| Diisopropyl ether | 0.40 | 2.5 |
| Butyl ethyl ether | 0.49 | 2.7 |
| Benzyl formate | 0.46 | 2.6 |
| Heptyl formate | 0.42 | 2.2 |

Table 1 above shows that 1-hexanol and 1-heptanol are especially suitable as extraction agents for extraction.

The distribution coefficient $C_{FA, org}/C_{FA, aqu}$ indicates the ratio of the concentration of formic acid in the organic phase of the respective extraction agent ($C_{FA, org}$) to the concentration of formic acid in the aqueous phase ($C_{FA, aqu}$). The larger the distribution coefficient with the respective extraction agent, the greater the capacity of the respective extraction agent for holding formic acid and the better the extraction agent for extraction of formic acid from the aqueous phase. The selectivity $K_{FA}/K_{water}$ indicates the ratio of the distribution coefficients of formic acid and water. The greater the selectivity, the greater the amounts of catalyst and of substrate remaining in the aqueous phase. An extraction agent is thus more suitable the higher the distribution coefficient and the higher the selectivity of the respective extraction agent.

In another exemplary embodiment, the question of whether the extraction agent can be added to the reaction mixture during the oxidation of an organic substance to produce formic acid in order to achieve in situ extraction of formic acid during the oxidation reaction was investigated. The reaction mixture there contained 4.5 g glucose, 1.82 g (1 mmol) $H_8[PV_5Mo_7O_{40}]$ dissolved in 100 mL water plus 100 g of the respective extraction agent. The reaction was carried out at 90° C. and an oxygen partial pressure of 20 bar at various stirring speeds for six hours. During the reaction, the glucose was converted to formic acid and $CO_2$. The total carbon yield in the form of formic acid and $CO_2$, based on the amount of carbon used originally and the ratio of the molar amounts of formic acid produced to the molar amounts of $CO_2$ produced, was determined by gas chromatography and $^1$H-NMR using benzene as the external standard. The total carbon yield is given in mol %, based on the total moles of carbon used.

TABLE 2

| Stirring speed (rpm) | Extraction agent | Total carbon yield FA + $CO_2$ (mol % based on mol C used) | SelectivityFA (mol): $CO_2$ (mol) | Distribution coefficient K $c_{FA, org}/c_{FA, aqu}$ |
|---|---|---|---|---|
| 600 | 1-hexanol | 25 | 88:12 | 0.88 |
| 600 | 1-heptanol | 59 | 89:11 | 0.59 |
| 800 | 1-hexanol | 16 | 80:20 | 0.69 |
| 800 | 1-heptanol | 44 | 81:19 | 0.54 |
| 1000 | 1-hexanol | 24 | 80:20 | 0.65 |
| 1000 | 1-heptanol | 40 | 82:18 | 0.55 |
| 1200 | 1-hexanol | 22 | 80:20 | 0.97 |
| 1200 | 1-heptanol | 37 | 78:22 | 0.60 |
| 1400 | 1-hexanol | 27 | 86:14 | 0.77 |
| 1400 | 1-heptanol | 43 | 82:18 | 0.67 |
| 1000 | no extraction agent | 100 | 53:47 | — |

The results shown in Table 2 above illustrate that the presence of the extraction agent led to a great increase in the selectivity for formic acid with the reaction products obtained here, i.e., of the reaction products formic acid and $CO_2$ formed in the reaction, the amount of formic acid in the reaction products is greatly increased. However, this increased selectivity is associated with a lower conversion rate, regardless of the stirring speed, i.e., the oxidation of glucose proceeds more slowly in the system containing the extraction agent than in a system without the extraction agent. In additional experiments, it was discovered that the increased selectivity is not a result of the slower glucose oxidation but instead is a result of highly effective extraction of formic acid in the biphasic reaction system.

This experiment shows that the reaction of an organic substance to formic acid triggered by the catalyst is in fact inhibited by the extraction agent, but this inhibition is at least partially compensated by a greater selectivity in favor of formic acid.

What is claimed is:

1. A method for separating formic acid from a reaction mixture comprising in addition to formic acid a polyoxometalate ion of the general formula $[PMo_xV_yO_{40}]^{n-}$, wherein $6 \leq x \leq 11$, $1 \leq y \leq 6$, $x+y=12$ and $3<n<10$, wherein n, x and y are each integers, the separation being accomplished by extraction by means of a linear primary alcohol, wherein the carbon chain of the alcohol has five to twelve carbon atoms, and the reaction mixture is in a protic solvent.

2. The method according to claim 1, wherein the linear primary alcohol has six, seven or eight carbon atoms.

3. The method according to claim 1, wherein the linear primary alcohol comprises 1-hexanol or 1-heptanol.

4. The method according to claim 1, wherein the protic solvent is an organic substance or the reaction mixture comprises an organic substance.

5. The method according to claim 4, wherein the organic substance is an α-hydroxyaldehyde, an α-hydroxycarboxylic acid, a carbohydrate or a glycoside.

6. The method according to claim 1, wherein the protic solvent is polar.

7. The method according to claim 1, wherein the protic solvent is water.

8. The method according to claim 1, wherein the linear primary alcohol is separated from at least a portion of the formic acid after extraction and added to the reaction mixture for further extraction of formic acid.

9. The method according to claim 1, wherein $n=3+y$.

10. The method according to claim 1, wherein the separation takes place by extraction during a reaction to produce formic acid.

11. The method according to claim 10, wherein the separation takes place at a temperature of 50° C. to 120° C.

* * * * *